(12) United States Patent
Dakka et al.

(10) Patent No.: US 9,024,078 B2
(45) Date of Patent: May 5, 2015

(54) DEHYDROGENATION PROCESS

(75) Inventors: Jihad M. Dakka, Whitehouse Station, NJ (US); Lorenzo C. Decaul, Langhorne, PA (US); Sabato Miseo, Pittstown, NJ (US); James R. Lattner, LaPorte, TX (US); Tan-Jen Chen, Kingwood, TX (US); Terry E. Helton, Bethlehem, PA (US); Teng Xu, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 13/515,104

(22) PCT Filed: Dec. 17, 2010

(86) PCT No.: PCT/US2010/061037
§ 371 (c)(1),
(2), (4) Date: Aug. 17, 2012

(87) PCT Pub. No.: WO2011/096997
PCT Pub. Date: Aug. 11, 2011

(65) Prior Publication Data
US 2012/0302798 A1 Nov. 29, 2012

Related U.S. Application Data

(60) Provisional application No. 61/301,786, filed on Feb. 5, 2010.

(51) Int. Cl.
| | | |
|---|---|---|
| *C07C 37/08* | (2006.01) | |
| *C07C 5/32* | (2006.01) | |
| *C07C 37/07* | (2006.01) | |
| *C07C 45/53* | (2006.01) | |
| *C07C 407/00* | (2006.01) | |

(52) U.S. Cl.
CPC ............... *C07C 37/08* (2013.01); *C07C 37/07* (2013.01); *C07C 45/53* (2013.01); *C07C 407/00* (2013.01); *C07C 2101/14* (2013.01); *C07C 2523/42* (2013.01)

(58) Field of Classification Search
USPC .......................................... 568/798; 585/379
See application file for complete search history.

(56) References Cited

U.S. PATENT DOCUMENTS

| | | |
|---|---|---|
| 3,358,044 A | 12/1967 | Russell et al. |
| 3,514,492 A | 5/1970 | Juguin et al. |
| 3,519,575 A | 7/1970 | Bozik et al. |
| 3,534,116 A | 10/1970 | Fuller |
| 3,580,970 A | 5/1971 | Swift |
| 3,691,102 A | 9/1972 | Swift |
| 3,879,446 A * | 4/1975 | Blood et al. ............... 560/214 |
| 3,962,362 A | 6/1976 | Suggitt |
| 4,016,049 A | 4/1977 | Fozzard et al. |
| 4,019,965 A | 4/1977 | Fozzard |
| 4,021,490 A | 5/1977 | Hudson |
| 4,115,204 A | 9/1978 | Murtha et al. |
| 4,115,205 A | 9/1978 | Murtha |
| 4,115,206 A | 9/1978 | Murtha |
| 4,115,207 A | 9/1978 | Murtha |
| 4,167,456 A | 9/1979 | Murtha |
| 4,169,857 A | 10/1979 | Murtha |
| 4,177,218 A * | 12/1979 | Antos ........................ 585/379 |
| 4,201,632 A | 5/1980 | Murtha |
| 4,218,346 A * | 8/1980 | Walker et al. ............. 502/343 |
| 4,219,447 A * | 8/1980 | Wheelock .................. 502/333 |
| 4,230,638 A | 10/1980 | Murtha |
| 4,258,268 A | 3/1981 | Bjornson |
| 4,417,076 A * | 11/1983 | Rozovsky et al. ........... 568/361 |
| 4,929,762 A | 5/1990 | Matsunaga et al. |
| 4,933,507 A | 6/1990 | Inoki et al. |
| 5,147,837 A * | 9/1992 | Dessau et al. ................ 502/66 |
| 5,256,348 A | 10/1993 | Waller |
| 5,395,976 A | 3/1995 | Scharschmidt et al. |
| 2009/0206004 A1 | 8/2009 | McCarthy et al. |

FOREIGN PATENT DOCUMENTS

| | | | | |
|---|---|---|---|---|
| EP | 0 316 142 | | 5/1989 | |
| FR | 1509921 | | 1/1968 | |
| JP | 2009-084227 | * | 4/2009 | ............... C07C 4/18 |
| WO | 2009/131769 | | 10/2009 | |
| WO | WO2009131769 | * | 10/2009 | ............... C07C 2/74 |
| WO | 2011/096992 | | 8/2011 | |
| WO | 2011/096993 | | 8/2011 | |
| WO | 2011/096999 | | 8/2011 | |

OTHER PUBLICATIONS

Translation of JP2009-084227.*
Saito, "Performance of Activity Test on Supported Pd Catalysts for Dehydrogenation of Cyclohexanone to Phenol (Effect of Supports on the Activity)", Ibaraki Kogyo Koto Senmon Gakko Kenkyu Iho (1995), 30, pp. 39-46. (Abstract).
Arends, "Selective Catalytic Oxidation of Cyclohexylbenzene to Cyclohexylbenzene-1-hydroperoxide: a coproduct-free route to phenol", Tetrahedron 58, (2002) pp. 9055-9061.

* cited by examiner

*Primary Examiner* — Paul A Zucker
*Assistant Examiner* — Mark Luderer

(57) ABSTRACT

A dehydrogenation process for the dehydrogenation of at least one dehydrogenatable hydrocarbon, the process comprising contacting a feed comprising the at least one dehydrogenatable hydrocarbon under dehydrogenation conditions with a catalyst composition comprising a support and at least one dehydrogenation component wherein said conditions include a temperature of from 400° C. to 750° C. and a pressure of at least 50 psig (345 kPag).

22 Claims, 1 Drawing Sheet

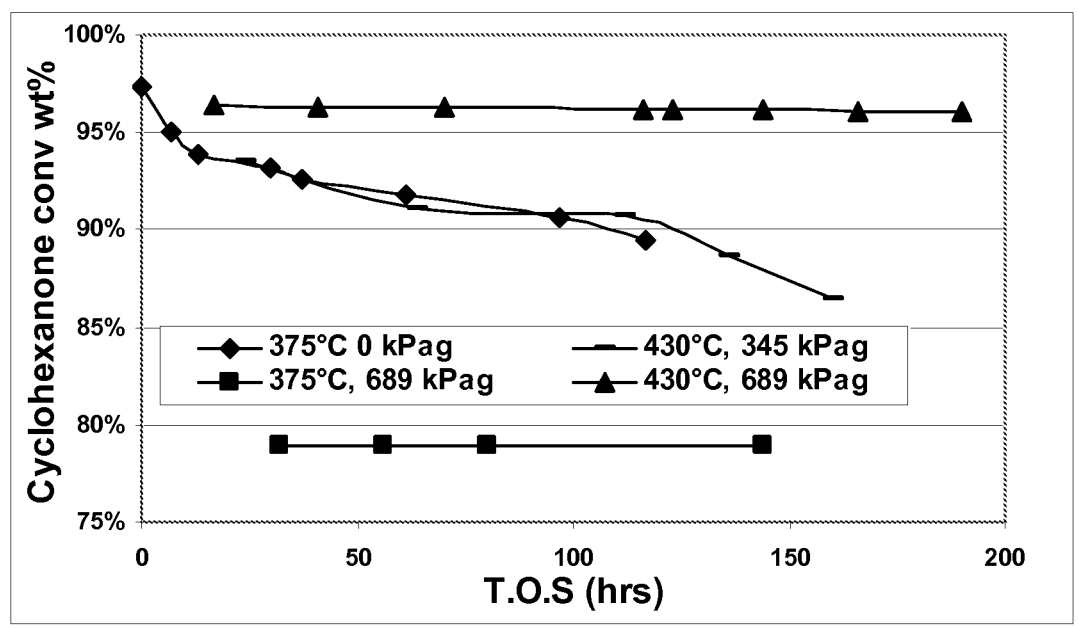

DEHYDROGENATION PROCESS

PRIORITY CLAIM

This application is a National Stage Application of International Application No. PCT/US2010/061037 filed Dec. 17, 2010, which claims priority to U.S. Provisional Application Ser. No. 61/301,786 filed Feb. 5, 2010, the disclosures of which are fully incorporated herein by their reference.

CROSS REFERENCE TO RELATED APPLICATIONS

This patent application is related to U.S. Provisional application Ser. No. 61/301,780, filed Feb. 5, 2010; U.S. Provisional application Ser. No. 61/301,794, filed Feb. 5, 2010; and U.S. Provisional application Ser. No. 61/301,799, filed Feb. 5, 2010 the disclosures of which are fully incorporated herein by their reference.

FIELD

The present invention relates to a dehydrogenation process, specifically optimum operating conditions for the dehydrogenation of a dehydrogenatable hydrocarbon such as cyclohexanone.

BACKGROUND

Various dehydrogenation processes have been proposed to dehydrogenate dehydrogenatable hydrocarbons such as cyclohexanone and cyclohexane. For example, these dehydrogenation processes have been used to convert at least a portion of the cyclohexanone into phenol.

Phenol is an important product in the chemical industry and is useful in, for example, the production of phenolic resins, bisphenol A, ε-caprolactam, adipic acid, and plasticizers.

Currently, the most common route for the production of phenol is the Hock process. This is a three-step process in which the first step involves alkylation of benzene with propylene to produce cumene, followed by oxidation of the cumene to the corresponding hydroperoxide and then cleavage of the hydroperoxide to produce equimolar amounts of phenol and acetone.

Other known routes for the production of phenol involve the direct oxidation of benzene, the oxidation of toluene, and the oxidation of s-butylbenzene wherein methyl ethyl ketone is co-produced with phenol in lieu of acetone produced in the Hock process.

Additionally, phenol can be produced by the oxidation of cyclohexylbenzene to cyclohexylbenzene hydroperoxide wherein cyclohexanone is co-produced with phenol in lieu of acetone produced in the Hock process. A producer using this process may desire to dehydrogenate at least a portion of the cyclohexanone produced into additional phenol depending on market conditions.

There are many methods for dehydrogenating various compounds into phenol. For example, U.S. Pat. No. 4,933,507 discloses that phenol can be produced by dehydrogenating cyclohexenone through a vapor-phase reaction in the presence of hydrogen using a solid-phase catalyst having platinum and an alkali metal carried on a support such as silica, silica-alumina or alumina. In addition, Saito et al. disclose the use of palladium supported on various metal oxides ($Al_2O_3$, $TiO_2$, $ZrO_2$, MgO) as a catalyst in the dehydrogenation of cyclohexanone to phenol. See "Performance of Activity Test on Supported Pd Catalysts for Dehydrogenation of Cyclohexanone to Phenol (effect of supports on activity)," *Ibaraki Kogyo Koto Senmon Gakko Kenkyu Iho* (1995), 30, pp. 39-46.

One problem that has been encountered in the use of dehydrogenation catalyst compositions in the dehydrogenation of dehydrogenatable compounds such as cyclohexanone is that the activity of the dehydrogenation component, such as a noble metal, decreases fairly rapidly. Accordingly, there is a need for a cyclohexanone dehydrogenation catalyst having improved resistance to deactivation.

According to the present invention, it has now been found that the stability of a dehydrogenation catalyst may be improved by operating dehydrogenation process at a pressure above 50 psig (345 kPag).

SUMMARY

In one aspect, the invention resides in a process for the dehydrogenation of at least one dehydrogenatable hydrocarbon, the process comprising contacting a feed comprising the at least one dehydrogenatable hydrocarbon under dehydrogenation conditions with a catalyst composition comprising a support and a dehydrogenation component wherein said conditions include a temperature of from 250° C. to 750° C. and a pressure of at least 50 psig (345 kPaG).

Conveniently, the process will produce a fully or partially dehydrogenated hydrocarbon.

Conveniently, the catalyst composition may comprise: (i) a support; (ii) a dehydrogenation component comprising at least one metal component selected from Groups 6 to 10 of the Periodic Table of Elements; and (iii) an inorganic base component comprising at least one metal component selected from Group 1 and Group 2 of the Periodic Table of Elements.

Conveniently, the catalyst may be produced by a method comprising treating the support with a liquid composition comprising said dehydrogenation component or a precursor thereof and at least one organic dispersant selected from an amino alcohol and an amino acid.

Conveniently, the invention resides in a catalyst composition comprising: (i) a support; (ii) a dehydrogenation component comprising at least one metal component selected from Groups 6 to 10 of the Periodic Table of Elements; and (iii) an inorganic base component comprising at least one metal component selected from Group 1 and Group 2 of the Periodic Table of Elements, wherein said catalyst composition exhibits oxygen chemisorption of greater than 30%.

Conveniently, the at least one dehydrogenatable hydrocarbon is an alicyclic compound such as cyclohexane and cyclohexanone wherein the at least one dehydrogenatable hydrocarbon is converted into an aromatic compound such as benzene and phenol.

Conveniently, the at least one dehydrogenatable hydrocarbon is cyclohexanone wherein at least a portion of cyclohexanone is converted into phenol.

Conveniently, the at least one dehydrogenatable hydrocarbon is cyclohexane wherein at least a portion of the cyclohexane is converted into benzene.

Conveniently, the support comprises at least one material selected from silica, a silicate, an aluminosilicate, a zirconia, carbon, and carbon nanotubes, and preferably comprises silica.

Conveniently, the dehydrogenation component comprises at least one metal component selected from platinum, palladium, and preferably comprises platinum.

In one embodiment, the inorganic base component is a metal component comprising potassium.

Typically, the dehydrogenation process conditions are capable of dehydrogenating cyclohexanone at an initial conversion of 95% or more.

In a further aspect, the invention resides in a process for producing phenol from benzene, the process comprising:

(a) contacting benzene and hydrogen with a catalyst under hydroalkylation conditions to produce cyclohexylbenzene;

(b) oxidizing at least a portion of cyclohexylbenzene from (a) to produce cyclohexylbenzene hydroperoxide;

(c) converting at least a portion of cyclohexylbenzene hydroperoxide from (b) to produce an effluent steam comprising phenol and cyclohexanone; and (d) contacting at least a portion of said effluent stream with a catalyst comprising a support and a dehydrogenation component under dehydrogenation conditions effective to convert at least a portion of the cyclohexanone in said feed into phenol and hydrogen, wherein the catalyst is produced by a method comprising treating the support with a liquid composition comprising said dehydrogenation component or a precursor thereof and at least one organic dispersant selected from an amino alcohol and an amino acid.

BRIEF DESCRIPTION OF THE DRAWINGS

FIG. 1 is a graph comparing cyclohexanone conversion against time on stream for the 1% K/0.8% Pt/SiO$_2$ catalyst of Example 1 at 2 hr$^{-1}$ weight hour space velocity (WHSV) with four different temperature and pressure conditions.

DETAILED DESCRIPTION

Described herein is a process for dehydrogenating at least one dehydrogenatable hydrocarbon such as cyclohexanone wherein the dehydrogenation process operates at a pressure of at least 50 psig (345 kPag). Specifically, this dehydrogenation process can be utilized in a phenol process wherein cyclohexanone is co-produced with phenol by allowing at least a portion of the co-produced cyclohexanone to be converted to additional phenol. In the phenol process wherein cyclohexanone is co-produced, cyclohexylbenzene, generally produced by the catalytic hydroalkylation of benzene, is oxidized to produce cyclohexylbenzene hydroperoxide and then the cyclohexylbenzene hydroperoxide is cleaved to produce an effluent stream comprising phenol and cyclohexanone in substantially equimolar amounts. At least a portion of the effluent is then fed to a dehydrogenation reaction zone, where the effluent stream portion is contacted with a dehydrogenation catalyst so as to convert the cyclohexanone in said effluent portion into additional phenol and into hydrogen wherein the hydrogen may be recycled to the benzene hydroalkylation step.

Dehydrogenation Process

The dehydrogenation process may be used to dehydrogenate any dehydrogenatable hydrocarbon such as an alicyclic compound. "Dehydrogenatable hydrocarbon" refers to all classes of hydrocarbons containing saturated carbon bonds which have the potential for forming one or more unsaturated bonds through the process of dehydrogenation. "Alicyclic compounds" refers to saturated or unsaturated non-aromatic hydrocarbon ring systems containing from three to twenty ring carbon atoms wherein the hydrocarbon ring system may also have a side-chain or a functional group attached directly to or bound within the ring. Examples of alicyclic compounds include, without limitation, cyclopropane, cyclopentane, methyl cyclopentane, cyclobutane, cyclopentene, cyclodecane, cyclohexane, methylcyclohexane, cyclododecane, and six carbon ring alicyclic compounds such as cyclohexane.

Other examples of alicyclic compounds include without limitation alicylic ketones such as cyclohexanone and alicylic alcohols such as cyclohexanol.

In one embodiment, at least a portion of the six carbon ring alicyclic compounds are dehydrogenated (or converted) to aromatic compounds such as benzene and phenol. For example, at least a portion of cyclohexanone may be dehydrogenated to phenol and at least a portion of cyclohexane may be dehydrogenated to benzene.

In another embodiment, at least a portion of the alicyclic compounds are (i) dehydrogenated to unsaturated compounds; (ii) rearranged to form other alicyclic compounds; or (iii) fragment to lighter hydrocarbons.

Unexpectedly, it has been found that operating at higher pressures (>50 psig), the catalyst remains stable, active, and selective. Suitable conditions for the dehydrogenation step include a temperature of about 250° C. to about 750° C., a pressure of about atmospheric to about 500 psi-gauge (psig) [100 to 3447 kPa-gauge (kPag)], a weight hourly space velocity of about 0.2 to 50 hr$^{-1}$, and a hydrogen to cyclohexanone-containing feed molar ratio of about 0 to about 20, optionally a hydrogen to cyclohexanone-containing feed molar ratio of about 0.1 to about 20.

In one embodiment, the operating temperature of the dehydrogenation process is from 200° C. to 750° C. Preferably, the operating temperature of the dehydrogenation process is from 300° C. to 750° C.; from 350° C. to 650° C.; from 400° C. to 550° C., from 450° C. to 550° C., and from 400° C. to 500° C. In other embodiments, the operating temperature lower limit may be 350° C., 400° C., 430° C., 440° C., 450° C., 460° C., 470° C., 480° C., 490° C.; and the upper limit temperature may be 500° C., 510° C., 520° C., 530° C., 540° C., 550° C., 600° C., 650° C., 700° C., and 750° C. with ranges from any lower limit to any upper limit being contemplated. In still other embodiments, the operating temperature lower limit may be 500° C., 510° C., 520° C., 530° C., 540° C., 550° C.; and the upper limit temperature may be 560° C., 570° C., 580° C., 590° C., 600° C., 650° C., 700° C., and 750° C. with ranges from any lower limit to any upper limit being contemplated.

In one embodiment, the operating pressure of the dehydrogenation process is from 0 to 500 psig or from 0 psig to 150 psig or from 0 psig to 125 psig. Preferably, the operating pressure of the dehydrogenation process is from 0 to 300 psig (0 to 2068 kPag), 50 to 300 psig (345 to 2068 kPag), from 60 to 300 psig (414 to 2068 kPag), from 70 to 300 psig (482 to 2068 kPag), from 80 to 300 psig (552 to 2068 kPag), from 90 to 300 psig (621 to 2068 kPag), and from 100 to 300 psig (689 to 2068 kPag). In other embodiments, the operating pressure lower limit may be 50 psig (345 kPag), 60 psig (414 kPag), 70 psig (482 kPag), 80 psig (552 kPag), 90 psig (621 kPa), 100 psig (689 kPag) and the upper limit operating pressure may be 125 psig (862 kPag), 150 psig (1034 kPag), 175 psig (1207 kPag), 200 psig (1379 kPag), 250 psig (1724 kPag), 300 psig (2068 kPag), 400 psig (2758 kPag), and 500 psig (3447 kPag) with ranges from any lower limit to any upper limit being contemplated. In still other embodiments, the operating pressure lower limit may be 150 psig (1034 kPag), 160 psig (1103 kPag), 170 psig (1172 kPag), 180 psig (1241 kPag), 190 psig (1310 kPag), 200 psig (1379 kPag); and the upper limit operating temperature may be 250 psig (1724 kPag), 300 psig (2068 kPag), 400 psig (2758 kPag), and 500 psig (3447 kPag) with ranges from any lower limit to any upper limit being contemplated.

The reactor configuration used for the dehydrogenation process generally comprises one or more fixed bed reactors containing a solid catalyst with a dehydrogenation function.

Provision can be made for the endothermic heat of reaction, preferably by multiple adiabatic beds with interstage heat exchangers. The temperature of the reaction stream drops across each catalyst bed, and then is raised by the heat exchangers. Preferably, 3 to 5 beds are used, with a temperature drop of 30° C. to 100° C. across each bed. Preferably the last bed in the series runs at a higher exit temperature than the first bed in the series.

In one embodiment, the dehydrogenation catalyst comprises a support, typically formed of silica, a silicate, an aluminosilicate, carbon, or carbon nanotubes, on which is deposited a dehydrogenation component. One type of aluminosilicate that may be used in as a support includes but is not limited to MCM-41.

In one embodiment, the dehydrogenation catalyst comprises a silica support having pore volumes and pore diameters determined by the method of mercury intrusion porosimetry described by ASTM Standard Test D4284. The silica support may have surface areas as measured by ASTM D3663. In one embodiment, the pore volumes are in the range from about 0.6 cc/gram to about 2.0 cc/gram or from about 1.0 cc/gram to about 1.5 cc/gram. The median pore diameters as measured by mercury are in the range from about 100 angstroms to about 2000 angstroms, more preferably from 200 angstroms to 500 angstroms or from 300 angstroms to 400 angstroms. The surface areas ($m^2$/gram) from 10 to 1000 $m^2$/gram or from 20 to 250 $m^2$/gram or from 50 to 200 $m^2$/gram or from 100 to 150 $m^2$/gram.

In one embodiment, the dehydrogenation component employed in the present catalyst comprises at least one metal component selected from Groups 6 to 10 of the Periodic Table of Elements, such as platinum and palladium, such that the dehydrogenation component may comprise any combination or mixture of metal components selected from Groups 6 to 10 of the Periodic Table of Elements. Typically, the dehydrogenation component is present in an amount between about 0.1 and about 10 wt % of the catalyst, preferably between 0.1 and 5 wt %, more preferably between 0.1 and 2 wt %. The term "metal component" is used herein to include a metal compound that may not be purely the elemental metal, but could, for example, be at least partly in another form, such as an oxide, hydride or sulfide form. The weight % (wt %) of the metal component is herein defined as being measured as the metal present based on the total weight of the catalyst composition irrespective of the form in which the metal component is present.

In another embodiment, the dehydrogenation catalyst comprises, in addition to the dehydrogenation component, an inorganic base component comprising at least one metal component selected from Group 1 and Group 2 of the Periodic Table of Elements, such as potassium, cesium, and rubidium, such that the inorganic base component may comprise a metal component selected from Group 1 and Group 2 of the Periodic Table of Elements. In one embodiment, the inorganic base component is present in an amount of at least 0.1 wt %, at least 0.2 wt %, at least 0.3 wt %, at least 0.4 wt % and at least 0.5 wt %. Typically, the inorganic base component is present in an amount between about 0.1 and about 5 wt % of the catalyst, preferably between 0.1 and 3 wt %, more preferably between 0.1 and 2 wt % of the catalyst. The weight % (wt %) of the dehydrogenation or base "component" is herein defined as being measured as the metal present based on the total weight of the catalyst composition irrespective of the form in which the metal component is present.

In one embodiment, the dehydrogenation catalyst may be produced by initially treating the support, such as by impregnation, with a solution of the dehydrogenation component or a precursor thereof. After drying, the treated support may be calcined, normally in an oxygen-containing atmosphere, such as air, at a temperature of about 100° C. to about 700° C. for a time of about 0.5 to about 50 hours. The calcined support may then be treated, again typically by impregnation, with a solution of the inorganic base component or a precursor thereof. After treatment with the inorganic base component, the support is again dried and calcined, normally in an oxygen-containing atmosphere, such as air, at a temperature of about 100° C. to about 700° C. for a time of about 0.5 to about 50 hours.

In another embodiment, the dehydrogenation catalyst may be produced by initially treating the support, such as by impregnation, with a solution of the inorganic base component, such as an aqueous solution of potassium carbonate. After drying, the treated support may be calcined, normally in an oxygen-containing atmosphere, such as air, at a temperature of about 100° C. to about 700° C. for a time of about 0.5 to about 50 hours. The calcined support may then be treated, again typically by impregnation, with a solution of the dehydrogenation component or a precursor thereof. After treatment with the dehydrogenation component, the support is again dried and calcined, normally in an oxygen-containing atmosphere, such as air, at a temperature of about 100° C. to about 700° C. for a time of about 0.5 to about 50 hours.

In an alternative embodiment, the dehydrogenation catalyst is produced by initially treating the support, such as by impregnation, with a solution containing both the dehydrogenation component and the inorganic base component or a precursor thereof, optionally together with at least one organic dispersant selected from an amino alcohol and an amino acid. In this case, after drying, a single calcination procedure, normally in an oxygen-containing atmosphere, such as air, at a temperature of about 100° C. to about 700° C. for a time of about 0.5 to about 50 hours, is used to produce the finished catalyst.

In one embodiment, the catalyst employed in the dehydrogenation reaction comprises: (i) a support; (ii) a dehydrogenation component; and (iii) an inorganic base component may exhibit oxygen chemisorption of greater than 10%, 30%, and 50%; preferably greater than 60%; and more preferably greater than 70%, depending on the method employed in manufacturing the catalyst.

In still another embodiment, the dehydrogenation catalyst is prepared by initially treating the support, normally by impregnation, with a liquid composition comprising the dehydrogenation component or a precursor thereof, an optional inorganic base component or a precursor thereof, and at least one organic dispersant selected from an amino alcohol and an amino acid. The organic dispersant may be dispersed in a liquid carrier. The liquid carrier is generally water. Examples of amino alcohols include wherein the amino alcohol is selected from the group consisting of methanolamine, dimethanolamine, tr-methanolamine, ethanolamine, di-ethanolamine, triethanolamine, butanolamine, dibutanolamine, tributanolamine, propanolamine, dipropanaolamine, tripropanolamine, N,N,-dialkyl-ethanolamines, N-alkyl-diethanolamines, N-alkyl-ethanolamines, N,N,-dialkyl-propanolamines, N-alkyl-dipropanolamines, N-alkyl-propanolamines, N,N,-dialkyl-propanolamines, N,N,-dialkyl-butonolamines, N-alkyl-dibutanolamines, N-alkyl-butanolamines, N,N,-dialkyl-butanolamines, N-alkyl-dibutanolamines, N-alkyl-butanolamines, N,N,-dialkyl-hexanolamines, N-alkyl-dihexanolamines, N-alkyl-hexanolamines, N,N,-dialkyl-hexanolamines, N-alkyl-dihexanolamines, N-alkyl-hexanolamines, N,N,-dialkyl-heptanolamines, N-alkyl-diheptanolamines, N-alkylheptanolamines, N,N,-dialkyl-heptanolamines, N-alkyl-diheptanolamines, N-alkyl-heptanolamines Examples of amino acids include alanine, arginine, asparagines, aspartic acid, cysteine, cystine, 3,5-dibromotyrosine, 3,5, diiodotyrosine, glutamic acid, glutamine, glycine, histidine, hydroxylysine, hydroxyproline, isoleucine, leucine, lysine, methionine, phenylalanine, proline, serine, threonine, thyroxine, tryptophane, tyrosine and valine, with arginine being preferred.

Generally, the organic dispersant is present in the liquid composition in an amount between about 1 and about 20 wt % of the composition. After treatment with the liquid composition, the support is dried to remove the liquid carrier and is then heated in an oxidizing atmosphere, generally in air, under conditions to decompose substantially all of said organic dispersant. Suitable conditions for removing the dispersant include a temperature of about 100° C. to about 600° C. for a time of about 0.5 to about 50 hours. The catalyst may then be heated in a reducing atmosphere, such as hydrogen, at a temperature of about 50° C. to about 500° C. for a time of about 0.5 to about 10 hours to reduce the dehydrogenation component.

The dehydrogenation catalyst used herein may exhibit oxygen chemisorption of greater than 10%, 30%, 50%, 60%, and greater than 70%, depending on the method employed in manufacturing the catalyst.

As used herein, the oxygen chemisorption value of a particular catalyst is a measure of metal dispersion on the catalyst and is defined as [the ratio of the number of moles of atomic oxygen sorbed by the catalyst to the number of moles of dehydrogenation metal contained by the catalyst]×100%. The oxygen chemisorption values referred to herein are measured using the following technique.

Chemisorption measurements are obtained under static high vacuum conditions on a Quantachrome Autosorb 1A instrument. Approximately 0.3-0.5 grams of catalyst are loaded into a quartz cell and dried in flowing helium (He) by heating at 4° C./min to 130° C. and holding for 1 hour. The flow is then switched to hydrogen and the catalyst is reduced in flowing hydrogen by heating at 2° C./min to 425° C., holding isothermal for 2 hours, and then cooling to 400° C. in flowing hydrogen. Following reduction, the sample is evacuated (while still at 400° C.) with a turbomolecular pump for 30 minutes to remove any chemisorbed hydrogen. With the sample still under vacuum, the temperature is lowered to 40° C. and held isothermal during subsequent experiments. An 8-point isotherm (with pressures between 80 and 400 torr [between 10 and 53 kPa]) is measured at 40° C. with oxygen ($O_2$) as the adsorbent molecule. Extrapolation of the linear portion of this curve to zero pressure gives the total or combined adsorption uptake.

Production of Cyclohexylbenzene

The cyclohexylbenzene employed in the present process can be produced by any conventional technique, including alkylation of benzene with cyclohexene in the presence of an acid catalyst, such as zeolite beta or an MCM-22 family molecular sieve, or by oxidative coupling of benzene to biphenyl followed by hydrogenation of the biphenyl. However, in practice, the cyclohexylbenzene is generally produced by contacting benzene with hydrogen under hydroalkylation conditions in the presence of a hydroalkylation catalyst whereby the benzene undergoes the following reaction (1) to produce cyclohexylbenzene (CHB):

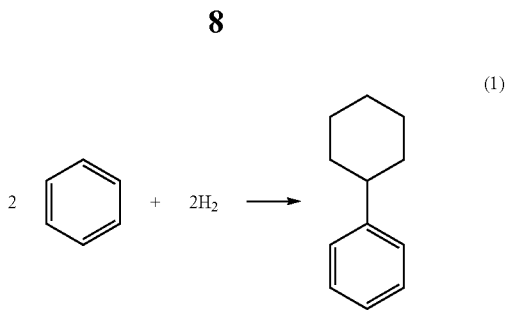

Details of such a process for producing cyclohexylbenzene can be found in paragraphs [0027] through [0038] of WO 2009/131769, the disclosure of which is hereby incorporated by reference.

Cyclohexylbenzene Oxidation

In order to convert the cyclohexylbenzene into phenol and cyclohexanone, the cyclohexylbenzene is initially oxidized to the corresponding hydroperoxide. This is accomplished by introducing an oxygen-containing gas, such as air, into a liquid phase containing the cyclohexylbenzene. Unlike cumene, atmospheric air oxidation of cyclohexylbenzene in the absence of a catalyst is very slow and hence the oxidation is normally conducted in the presence of a catalyst.

Details of such a process for producing cyclohexylbenzene can be found in paragraphs [0048] through [0055] of WO 2009/131769, the disclosure of which is hereby incorporated by reference.

Hydroperoxide Cleavage

The final reactive step in the conversion of the cyclohexylbenzene into phenol and cyclohexanone involves cleavage of the cyclohexylbenzene hydroperoxide, which is conveniently effected by contacting the hydroperoxide with a catalyst in the liquid phase at a temperature of about 20° C. to about 150° C., such as about 40° C. to about 120° C., a pressure of about 50 to about 2,500 kPa, such as about 100 to about 1000 kPa. The cyclohexylbenzene hydroperoxide is preferably diluted in an organic solvent inert to the cleavage reaction, such as methyl ethyl ketone, cyclohexanone, phenol or cyclohexylbenzene, to assist in heat removal. The cleavage reaction is conveniently conducted in a catalytic distillation unit.

Details of such a process for hydroperoxide cleavage can be found in paragraphs [0056] through [0075] of WO 2009/131769, the disclosure of which is hereby incorporated by reference.

Treatment of Cleavage Effluent

The effluent from the cleavage reaction comprises phenol and cyclohexanone in substantially equimolar amounts. The present process provides an advantageous route to increasing the amount of phenol produced from the original benzene feed by contacting at least a portion of the cleavage effluent with a dehydrogenation catalyst so as to convert some or all of the cyclohexanone in the effluent into additional phenol according to the reaction (2):

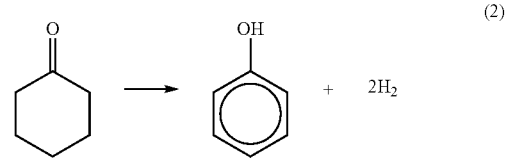

In one embodiment, the dehydrogenation catalyst and process described herein may be used in reaction (2).

Cyclohexanone and phenol produce an azeotropic mixture composed of 28 wt % cyclohexanone and 72 wt % phenol, so that any attempt to separate the effluent from the cyclohexylbenzene hydroperoxide cleavage step by simple distillation results in this azeotropic mixture. However, the efficiency of the separation can be enhanced by conducting the distillation under at least partial vacuum, typically at below 101 kPa. Moreover, extractive distillation processes are known for separating cyclohexanone and phenol, see for example, U.S. Pat. Nos. 4,021,490; 4,019,965; 4,115,207; 4,115,204; 4,115,206; 4,201,632; 4,230,638; 4,167,456; 4,115,205; and 4,016,049. Nevertheless, phenol/cyclohexanone separation remains a costly process, so that in one embodiment, the feed to the dehydrogenation step has the same composition as the cleavage effluent, thereby avoiding the need for an initial expensive separation step. Depending on the efficiency of the cyclohexanone dehydrogenation, the final product may contain substantially all phenol, thereby at least reducing the problem of separating the phenol from the cleavage effluent.

In another embodiment, the cleavage effluent is subjected to one or more separation processes to recover or remove one or more components of the effluent prior to dehydrogenation. In particular, the cleavage effluent is conveniently subjected to at least a first separation step to recover some or all of the phenol from the effluent, typically so that the effluent stream fed to said dehydrogenation reaction contains less than 50 wt %, for example less than 30 wt %, such as less than 1 wt %, phenol. The first separation step is conveniently effected by vacuum distillation and the same, or additional vacuum distillation steps, can be used to remove components boiling below 155° C. (as measured at 101 kPa), such as benzene and cyclohexene, and/or components boiling above 185° C. (as measured at 101 kPa), such as 2-phenyl phenol and diphenyl ether, prior to feeding the effluent stream to the dehydrogenation reaction.

By employing the present dehydrogenation process, substantially all the cyclohexanone in the cyclohexylbenzene hydroperoxide cleavage effluent can be converted to phenol. In practice, however, depending on market conditions, there is likely to be a significant demand for cyclohexanone product. This can readily met using the present process by reliance on the reversible nature of the reaction (2), namely by hydrogenating at least some of the phenol back to cyclohexanone. This can readily be achieved by, for example, contacting the phenol with hydrogen in the presence of a hydrogenation catalyst, such as platinum or palladium, under conditions including a temperature of about 20° C. to about 250° C., a pressure of about 101 kPa to about 10000 kPa and a hydrogen to phenol molar ratio of about 1:1 to about 100:1.

The invention will now be more particularly described with reference to the following non-limiting Examples and the accompanying drawing.

EXAMPLE 1

Catalyst Preparation 0.8 wt % Pt-1 wt % K/SiO2

0.403 grams hexachloro platonic acid was dissolved in 25 cc (4:1 wt ratio acetone/water). This solution was added to 20 grams of SiO2 extrudate (surface area of 130 m$^2$/gram, 300-400 Å pore diameter). The mixture was left overnight at room temperature to evaporate excess water. The metal impregnated catalyst was then dried at 100° C. Then 25 grams of a potassium carbonate solution (0.71 grams potassium carbonate in acetone/water 4:1 wt ratio) was added to the Pt/SiO2 extrudate sample. The mixture was left overnight at room temperature to evaporate water. Then it was dried at 100° C. This catalyst had approximately 0.8 wt % Pt and 1 wt % K.

Cyclohexanone Dehydrogenation

The reactor used in these experiments consists of a stainless steel tube with dimensions of 22 in. (56 cm) long×½ in. (1.3 cm) o.d.×0.035 in. (0.09 cm) wall thickness. A piece of stainless steel tubing 8¾ in. (22.2 cm) long×⅜ in. (0.95 cm) o.d and a piece of ¼ in. (0.635 cm) tubing of similar length was used in the bottom of the reactor as a spacer (one inside of the other) to position and support the catalyst in the isothermal zone of the furnace. A ¼ in. (0.635 cm) plug of glass wool was placed at the top of the spacer to keep the catalyst in place. A ⅛ in. (0.32 cm) stainless steel thermo-well was placed in the cat bed, long enough to monitor temperature throughout the catalyst bed using a movable thermocouple.

The catalyst was pressed into pellets then crushed and sized to 20-40 US sieve mesh. Typically 5.0 grams, vol. 12.5 cc. of the catalyst was pre-sized to 20-40 mesh and used as a standard loading. The catalyst was then loaded into the reactor from the top. The catalyst bed typically was 15 cm. in length. A ¼ in. (6.32 mm) plug of glass wool was placed at the top of the catalyst bed to separate quartz chips from the catalyst. The remaining void space at the top of the reactor was filled with quartz chips. The reactor was installed in the furnace with the catalyst bed in the middle of the furnace at the pre marked isothermal zone. The reactor was then pressure and leak tested typically at 300 psig (2068 kPag).

The catalyst was pre-conditioned in situ; heated to 375° C. to 430° C. with H2 flow at 100 cc/min and held for 2 hrs. A 500 cc ISCO syringe pump was used to introduce the cyclohexanone to the reactor. The feed was pumped through a vaporizer before flowing through heated lines to the reactor. A Brooks mass flow controller was used to set the hydrogen flow rate. A Grove "Mity Mite" back pressure controller was used to control the reactor pressure typically at 50 psig (345 kPag) to 100 psig (689 kPag) preferably at 100 psig (689 kPag). GC analyses were taken to verify feed composition. The feed was then pumped through the catalyst bed held at the reaction temperature of 375° C. to 430° C. preferably at 430° C. at a liquid hourly space velocity (LHSV) of 2 and a pressure of 100 psig (689 kPag). The products exiting the reactor flowed through heated lines routed to two collection pots in series. The non-condensable gas products routed to an on line HP 5890 GC. The first pot was heated to 60° C. and the second pot cooled with chilled coolant to about 10° C. The product was collected for material balances over 12 hrs to 24 hrs intervals. Samples were taken and diluted with 50% Ethanol for analysis. A Hewlett Packard 6890 gas chromatograph with flame ionization detector (FID) and with an Agilent technologies GC column 30 m×0.32 mm×0.25 micron film thickness was used for the analyses of the hydrocarbon products. Non-condensable gas products analyses were taken on line via a HP 5980 Gas Chromatograph with J and W Scientific column 60 m×0.25 mm ID×1.0 micron film. The HP 6890GC analysis ramp program was set to: 40° C. for 0 min; 5° C./min to 150° C., held 0 min; 10° C./min to 260° C., held 28 min total analysis time was 60 min; and the HP 5890 GC ramp was set to: −30° C. for 5 min, 5° C./min to 80° C. for 2 min, 5° C./min to 200° C. for 0 min, 15° C./min to 240° C. held to the end total analysis time was 60 min.

A typical time-on-stream (TOS) profile is shown for our inventive system in FIG. 1 wherein the process was ran at 2 hr$^{-1}$ WHSV at 4 different pressure and temperature conditions: (1) 375° C. and 0 psig (0 kPag); (2) 375° C. and 100 psig (689 kPag); (3) 430° C. and 50 psig (345 kPag); and (4) 430° C. and 100 psig (689 kPag).

EXAMPLE 2

The catalyst in this example was the same as the catalyst in Example 1 with only two differences: (i) the Pt loading is 1% rather than 0.8%; and (ii) tetra-ammine platinum nitrate rather than hexachloroplatinic acid was used as the platinum precursor.

This catalyst was tested over a wide range of reactor temperatures, ranging from 366° C. to 476° C. Weight hourly space velocity was kept constant at 2 hr$^{-1}$ WHSV. The hydrogen/cyclohexanone molar ratio of the feed was also kept constant, at 2. Reactor pressure was 100 psig. The data collected is presented in table 1 below.

TABLE 1

| Time-on-Stream, Days | Reactor Temperature, ° C. | Conversion, % |
|---|---|---|
| 1.8 | 473.0 | 98.3 |
| 4.8 | 457.3 | 97.4 |
| 5.7 | 441.8 | 95.8 |
| 6.7 | 424.5 | 93.0 |
| 9.2 | 398.7 | 84.0 |
| 12.5 | 373.2 | 70.3 |
| 13.7 | 474.0 | 97.5 |

As can be seen from the Table 1 above, conversion was 98.3% at day 1.8 when the reactor temperature was controlled at 473° C. Conversion dropped from 98.3% to 70.3% as reactor temperature was reduced from 473° C. to 373.2° C. More importantly, it was found that conversion was 97.5% when reactor temperature was adjusted back to 474° C. at 13.7 days-on-stream. This data once again illustrate that high stability can be obtained at high pressure in dehydrogenation of cyclohexanone to phenol.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

In another embodiment, this disclosure relates to:
1. A process for the dehydrogenation of at least one dehydrogenatable hydrocarbon, the process comprising contacting a feed comprising the at least one dehydrogenatable hydrocarbon under dehydrogenation conditions with a catalyst composition comprising a support and a dehydrogenation component wherein said conditions include a temperature of from 400° C. to 750° C. and a pressure of at least 50 psig (345 kPag).
2. The process of embodiment 1 wherein the at least one dehydrogenatable hydrocarbon is an alicyclic compound.
3. The process of embodiment 1, wherein the at least one dehydrogenatable hydrocarbon is cyclohexanone.
4. The process of embodiment 1, wherein said temperature is at least 450° C.
5. The process of embodiment 1, wherein said temperature is at least 460° C.
6. The process of embodiment 1, wherein said temperature is at least 470° C.
7. The process of embodiment 1, wherein said temperature is at least 500° C.
8. The process of embodiment 1, wherein said temperature is at least 550° C.
9. The process of embodiment 1, wherein said pressure is at least 75 psig (517 kPag).
10. The process of embodiment 1, wherein said pressure is at least 90 psig (621 kPag).
11. The process of embodiment 1, wherein said catalyst composition has an oxygen chemisorption of greater than 30%.
12. The process of embodiment 1, wherein the catalyst composition has an oxygen chemisorption of greater than 50%.
13. The process of embodiment 1, wherein the catalyst composition has an oxygen chemisorption of greater than 70%.
14. The process of embodiment 1, wherein the support comprises at least one material selected from silica, a silicate, an aluminosilicate, zirconia, carbon, and carbon nanotubes.
15. The process of embodiment 1, wherein the support comprises silica.
16. The process of embodiment 1, wherein the dehydrogenation component is at least one metal component selected from platinum and palladium.
17. The process of embodiment 1, wherein the dehydrogenation component is a metal component comprising platinum.
18. The process of embodiment 1, wherein dehydrogentable hydrocarbon is dehydrogenated at a conversion of 95% or more.
19. The process of embodiment 1, wherein said conditions further include introducing hydrogen to the process.
20. The process of embodiment 1, wherein said catalyst composition comprises: (i) a support; (ii) the dehydrogenation component comprising at least one metal component selected from Groups 6 to 10 of the Periodic Table of Elements; and (iii) an inorganic base component comprising at least one metal component selected from Group 1 and Group 2 of the Periodic Table of Elements; wherein said at least one metal component selected from Group 1 and Group 2 of the Periodic Table of Elements is present in an amount of at least 0.1 wt %.
21. The process of embodiment 20, wherein the inorganic base component is at least one metal component selected from potassium, cesium and rubidium.
22. The process of embodiment 20, wherein the inorganic base component is a metal component comprising potassium.
23. The process of any one of the preceding embodiments wherein said catalyst composition component comprises: (i) a support; (ii) the dehydrogenation component comprising at least one metal component selected from Groups 6 to 10 of the Periodic Table of Elements; and (iii) a inorganic base component comprising at least one metal component selected from Group 1 and Group 2 of the Periodic Table of Elements; wherein said at least one metal component selected from Group 1 and Group 2 of the Periodic Table of Elements is present in an amount of at least 0.1 wt %.
24. A process for producing phenol, the process comprising:
   (a) oxidizing cyclohexylbenzene to produce cyclohexylbenzene hydroperoxide;
   (b) converting at least a portion of cyclohexylbenzene hydroperoxide from (a) to produce an effluent stream comprising phenol and cyclohexanone; and
   (c) contacting at least a portion of said effluent stream with a catalyst composition comprising a support, a dehydrogenation component comprising at least one metal component selected from Groups 6 to 10 of the Periodic Table of Elements and a inorganic base component comprising at least one metal component selected from Group 1 and Group 2 of the Periodic Table of Elements under dehydrogenation conditions effective to convert at least a portion of the cyclohexanone in said feed into phenol and hydrogen;

wherein said dehydrogenation conditions include a temperature of at least 450° C. and a pressure of at least 90 psig (621 kPag).

25. The process of embodiment 24, wherein the at least a portion of said effluent stream in said contacting (c) has the same composition as the effluent stream produced in said converting (b).

The invention claimed is:

1. A process for the dehydrogenation of at least one dehydrogenatable hydrocarbon, the process comprising contacting a feed comprising the at least one dehydrogenatable hydrocarbon under dehydrogenation conditions with a catalyst composition free of germanium comprising a support and a dehydrogenation component comprising at least one metal component selected from platinum and palladium, wherein said conditions include a temperature of from 400° C. to 750° C. and a pressure of at least 50 psig, the catalyst composition has an oxygen chemisorption of greater than 50%.

2. The process of claim 1, wherein the at least one dehydrogenatable hydrocarbon is an alicyclic compound.

3. The process of claim 1, wherein the at least one dehydrogenatable hydrocarbon is cyclohexanone.

4. The process of claim 1, wherein said temperature is at least 450° C.

5. The process of claim 1, wherein said temperature is at least 460° C.

6. The process of claim 1, wherein said temperature is at least 470° C.

7. The process of claim 1, wherein said temperature is at least 500° C.

8. The process of claim 1, wherein said temperature is at least 550° C.

9. The process of claim 1, wherein said pressure is at least 75 psig.

10. The process of claim 1, wherein said pressure is at least 90 psig.

11. The process of claim 1, wherein the catalyst composition has an oxygen chemisorption of greater than 70%.

12. The process of claim 1, wherein the support is selected from the group consisting of silica, a silicate, an aluminosilicate, zirconia, carbon, and carbon nanotubes.

13. The process of claim 1, wherein the support comprises silica.

14. The process of claim 1, wherein the dehydrogenation component is a metal component comprising platinum.

15. The process of claim 1, wherein the catalyst composition is capable of dehydrogenating the dehydrogenatable hydrocarbon at a conversion of 95% or more.

16. The process of claim 1, wherein said conditions further include introducing hydrogen to the process.

17. The process of claim 1, wherein said catalyst composition further comprises an inorganic base component comprising at least one metal component selected from Group 1 and Group 2 of the Periodic Table of Elements wherein said at least one metal component selected from Group 1 and Group 2 of the Periodic Table of Elements is present in an amount of at least 0.1 wt %.

18. The process of claim 17, wherein the inorganic base component is at least one metal component selected from potassium, cesium and rubidium.

19. The process of claim 17, wherein the inorganic base component is a metal component comprising potassium.

20. The process of claim 1, wherein said catalyst composition comprises: (i) a support; (ii) the dehydrogenation component comprising at least one metal component selected from Groups 6 to 10 of the Periodic Table of Elements; and (iii) a inorganic base component comprising at least one metal component selected from Group 1 and Group 2 of the Periodic Table of Elements; wherein said at least one metal component selected from Group 1 and Group 2 of the Periodic Table of Elements is present in an amount of at least 0.1 wt %.

21. A process for producing phenol, the process comprising:
(a) oxidizing cyclohexylbenzene to produce cyclohexylbenzene hydroperoxide;
(b) converting at least a portion of cyclohexylbenzene hydroperoxide from (a) to produce an effluent stream comprising phenol and cyclohexanone; and
(c) contacting at least a portion of said effluent stream with a catalyst composition free of germanium comprising a support, a dehydrogenation component comprising at least one metal component comprising at least one metal component selected from platinum and palladium and an inorganic base component comprising at least one metal component selected from Group 1 and Group 2 of the Periodic Table of Elements under dehydrogenation conditions effective to convert at least at least a portion of the cyclohexanone in said feed into phenol and hydrogen;
wherein said dehydrogenation conditions include a temperature of at least 450° C. and a pressure of at least 90 psig, the catalyst composition has an oxygen chemisorption of greater than 50%.

22. The process of claim 21, wherein the at least a portion of said effluent stream in said contacting (c) has the same composition as the effluent stream produced in said converting (b).

* * * * *